US011898155B2

(12) United States Patent
Jinno et al.

(10) Patent No.: US 11,898,155 B2
(45) Date of Patent: Feb. 13, 2024

(54) METHOD FOR INTRODUCING MOLECULE AND COMPOSITION CONTAINING INHIBITOR

(71) Applicants: Pearl Kogyo Co., Ltd., Osaka (JP); i-Gene Corporation, Ehime (JP); National University Corporation Ehime University, Ehime (JP)

(72) Inventors: Masafumi Jinno, Matsuyama (JP); Yuki Isozaki, Mitoyo (JP); Yuto Kikuchi, Matsuyama (JP); Yugo Kido, Osaka (JP); Susumu Satoh, Tsukubamirai (JP)

(73) Assignees: PEARL KOGYO CO., LTD., Osaka (JP); I-GENE CORPORATION, Matsuyama (JP); NATIONAL UNIVERSITY CORPORATION EHIME UNIVERSITY, Matsuyama (JP)

( * ) Notice: Subject to any disclaimer, the term of this patent is extended or adjusted under 35 U.S.C. 154(b) by 585 days.

(21) Appl. No.: 16/770,496

(22) PCT Filed: Dec. 6, 2018

(86) PCT No.: PCT/JP2018/044958
§ 371 (c)(1),
(2) Date: Jun. 5, 2020

(87) PCT Pub. No.: WO2019/112014
PCT Pub. Date: Jun. 13, 2019

(65) Prior Publication Data
US 2021/0180088 A1 Jun. 17, 2021

(30) Foreign Application Priority Data
Dec. 7, 2017 (JP) ................................. 2017-235171

(51) Int. Cl.
*C12N 15/87* (2006.01)
*C12N 9/99* (2006.01)

(52) U.S. Cl.
CPC ............... *C12N 15/87* (2013.01); *C12N 9/99* (2013.01)

(58) Field of Classification Search
CPC .................... C12N 15/87; C12N 9/99
See application file for complete search history.

(56) References Cited

U.S. PATENT DOCUMENTS

| 2004/0110297 A1 | 6/2004 | Miyoshi et al. |
| 2005/0261221 A1 | 11/2005 | Wang et al. |
| 2011/0268750 A1 | 11/2011 | Mamoun et al. |
| 2016/0166636 A1 | 6/2016 | Muller et al. |
| 2017/0247672 A1 | 8/2017 | Chen |
| 2021/0195875 A1 | 7/2021 | Takano |

FOREIGN PATENT DOCUMENTS

| CN | 1501974 A | 6/2004 |
| CN | 104971348 A | 10/2015 |
| JP | 2011-517402 A | 6/2011 |
| JP | 2013-255475 A | 12/2013 |
| JP | 2014-507129 A | 3/2014 |
| JP | 2018-502071 A | 1/2018 |
| WO | 2012/087336 A1 | 6/2012 |
| WO | 2017/150566 A1 | 9/2017 |

OTHER PUBLICATIONS

International Search Report issued in corresponding International Patent Application No. PCT/JP2018/044958 dated Mar. 5, 2019.
Kikuchi et al., "Improvement in stability of plasma transgene by inhibition of autophagy pathway," Extended abstracts of the JSAP autumn meeting, 79: 18a-221C-7 (2018).
Sambrook et al., "Calcium-phosphate-mediated Transfection of Eukaryotic Cells with Plasmid DNAs," Molecular Cloning A Laboratory Manual, 3: 16.14-16.17, 16.27-16.31 (2001).
Hasegawa et al., "Microtubule involvement in the intracellular dynamics for gene transfecction mediated by cationic liposomes," Gene Therapy, 8 (21): 1669-1673 (2001).
Li et al., "The effect of nocodazole on the transfection efficiency of lipid-bilayer coated gold nanoparticles," Biomaterials, 30 (7): 1382-1388 (2009).
Apirakaramwong et al., "Mechanisms of Cellular Uptake with Chitosan/DNA Complex in Hepatoma Cell Line," Advanced Materials Research, 506: 485-488 (2012).
Jinno et al., "Investigation of plasma induced electrical and chemical factors and their contribution processes to plasma gene transfection," Archives of Biochemistry and Biophysics, 605: 59-66 (2016).
Lamb et al., "Endocytosis and autophagy: Shared machinery for degradation," Bioessays, 35 (1): 34-45 (2012).

(Continued)

*Primary Examiner* — Kevin E Weddington
(74) *Attorney, Agent, or Firm* — Morgan, Lewis & Bockius LLP

(57) ABSTRACT

Provided is a method for introducing a selected molecule, including: an inhibitor treatment step of allowing a target cell or a target tissue to internalizing an inhibitor of vesicular transport or lysosomal membrane fusion; and an introduction step of contacting an introduction liquid containing a selected molecule with the target cell or the target tissue to introduce the selected molecule into the target cell or the target tissue.

17 Claims, 13 Drawing Sheets

(56) References Cited

OTHER PUBLICATIONS

Jinno et al., "Synergistic effect of electrical and chemical factors on endocytosis in micro-discharge plasma gene transfection," Plasma Sources Science and Technology, 26 (6): 065016 (2017).
Extended European Search Report issued in corresponding European Patent Application No. 18884899.8 dated Nov. 5, 2021.
Office Action issued in counterpart Japanese Patent Application No. 2019-558283 dated Nov. 8, 2022.
Office Action dated Jun. 7, 2023, issued in corresponding Chinese Application No. 201880079087.2.

WITHOUT NOCODAZOLE TREATMENT (A)

(B)

(C)

1 μM NOCODAZOLE (A)

(B)

(C)

100 μM NOCODAZOLE (A)

(B)

(C)

(A)

(B)

WITHOUT NOCODAZOLE TREATMENT 1.0 μM NOCODAZOLE 0.1 μM NOCODAZOLE

WITHOUT NOCODAZOLE TREATMENT 1.0 μM NOCODAZOLE 0.1 μM NOCODAZOLE

WITHOUT NOCODAZOLE TREATMENT 1.0 μM NOCODAZOLE 0.1 μM NOCODAZOLE (A)

(B)

METHOD FOR INTRODUCING MOLECULE AND COMPOSITION CONTAINING INHIBITOR

TECHNICAL FIELD

The present invention relates to a method for introducing a selected molecule and a composition containing an inhibitor.

BACKGROUND ART

To elucidate intracellular molecular mechanisms, widely implemented are techniques for introducing, into a cell, a certain quantity of selected molecule such as an exogenous gene or a protein. Examples of the known technique for introducing a selected molecule into a cell include a biological technique using a virus, a physical technique such as electroporation or microinjection, a chemical technique such as lipofection, or a method using plasma (Patent Literature 1: Japanese Patent Laying-Open No. 2013-255475).

CITATION LIST

Patent Literature

PTL 1: Japanese Patent Laying-Open No. 2013-255475

SUMMARY OF INVENTION

Technical Problem

Nevertheless, there is still room for improvement in the efficiency of introduction into a cell with respect to the above method for introducing a selected molecule. Here, the present inventors have paid attention to the point where even when efficiently introduced into a cell, a selected molecule is degraded intracellularly and cannot fully exert a function of the selected molecule, often leading to a substantial decrease in the efficiency of introduction. Thus, it is desirable to provide an introduction method in which a selected molecule is stably present in a cell after introduction and can exert a function of the selected molecule highly efficiently.

The purpose of the invention is to provide a method for introducing a selected molecule so as to be able to improve the efficiency of introducing the selected molecule into a target cell or a target tissue.

Solution to Problem

[1] A method for introducing a selected molecule, including: an inhibitor treatment step of allowing a target cell or a target tissue to internalizing an inhibitor of an endocytosis- or autophagy-mediated lysosomal degradation pathway; and an introduction step of contacting an introduction liquid containing a selected molecule with the target cell or the target tissue to introduce the selected molecule into the target cell or the target tissue.

[2] The introduction method according to [1], wherein in the introduction step, the selected molecule is introduced via endocytosis into the target cell or the target tissue.

[3] The introduction method according to [1] or [2], wherein in the introduction step, the selected molecule is introduced by irradiating the target cell or the target tissue with plasma.

[4] The introduction method according to any one of [1] to [3], wherein the inhibitor is a low-molecular-weight compound permeable to a cell membrane of the target cell or a cell as a component of the target tissue.

[5] The introduction method according to [4], wherein the low-molecular-weight compound is at least one selected from the group consisting of nocodazole, chloroquine, LY-294002, and wortmannin.

[6] The introduction method according to any one of [1] to [5], wherein in the inhibitor treatment step, the target cell or the target tissue is allowed to internalize the inhibitor by contacting a composition containing the inhibitor with the target cell or the target tissue.

[7] A composition comprising the inhibitor, for use in the introduction method according to [6].

[8] The composition according to [7], wherein the composition is a culture medium for the target cell or the target tissue.

Advantageous Effects of Invention

The invention makes it possible to increase the efficiency of introducing a selected molecule into a target cell or a target tissue.

DESCRIPTION OF EMBODIMENTS

Hereinafter, embodiments of the invention will be described with reference to the drawings.

A method for introducing a selected molecule according to the invention includes: an inhibitor treatment step of allowing a target cell or a target tissue to internalizing an inhibitor of an endocytosis- or autophagy-mediated lysosomal degradation pathway; and an introduction step of contacting an introduction liquid containing a selected molecule with the target cell or the target tissue to introduce the selected molecule into the target cell or the target tissue.

[Inhibitor Treatment Step]

In an inhibitor treatment step in the invention, a target cell or tissue is allowed to internalize the above inhibitor. During the inhibitor treatment step, for instance, a composition containing an inhibitor may be contacted with a target cell or a target tissue (hereinafter, sometimes referred to as a "target cell, etc.") for an enough time for the target cell etc. to internalize the inhibitor. Specifically, it is possible to use a procedure in which a target cell, etc., is cultured in a culture medium (inhibitor-containing composition) such as a culture liquid or solid culture medium containing an inhibitor at a suitable concentration, a procedure in which after removal of a culture liquid, an inhibitor-containing aqueous solution (inhibitor-containing composition) is added to a container including a target cell, etc., or the like. The optimal conditions for the inhibitor treatment step differ depending on each inhibitor and each cell type. It is preferable that the inhibitor should not cause cell damage and the inhibitor effects are effective at the concentration. The treatment time is preferably from 1 min to 2 h and more preferably from 10 min to 60 min. The inhibitor treatment step may be before or after the introduction step. When the introduction of a selected molecule causes strong cell damage, the cell damage can be lowered by performing the inhibitor treatment step after the introduction step.

(Inhibitor)

Figure 1:
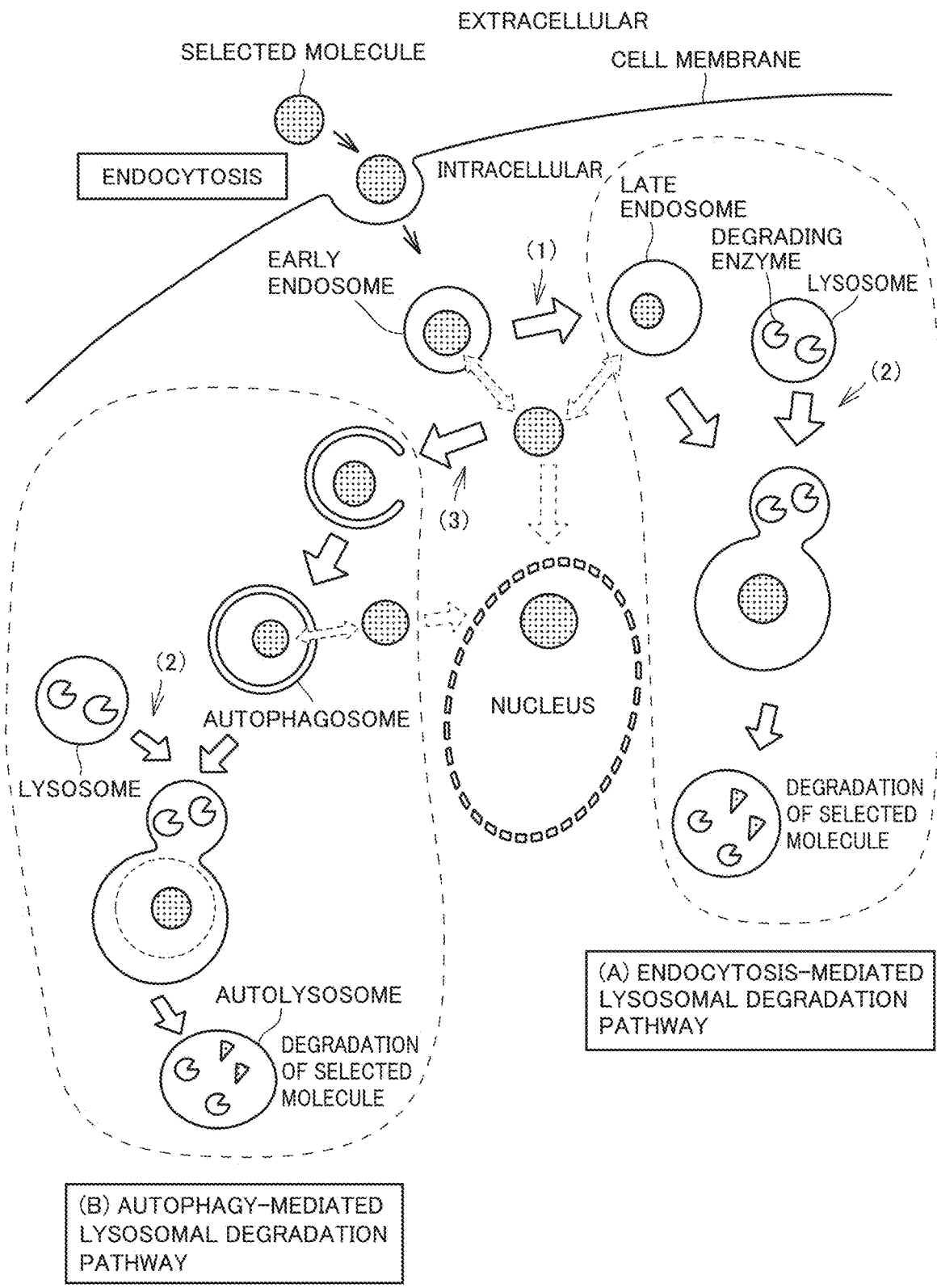
FIG. 1 is a schematic diagram illustrating an endocytosis- or autophagy-mediated lysosomal degradation pathway.

First, vesicular transport in a cell will be illustrated with reference to FIG. 1.

When selected molecules are introduced into cells, some of the selected molecules are taken up via endocytosis into the cell from the outside of the cell. The selected molecule-encapsulating vesicle is transported to an early endosome and is then matured (1) into a late endosome. Subsequently, the vesicle is subject to membrane fusion (2) with an acidic lysosome. The selected molecule is then degraded by a degrading enzyme included in the lysosome. Meanwhile, a selected molecule released into cytoplasm from the vesicle is enclosed by an autophagosome in cytoplasm (formation (3) of an autophagosome). Next, a lysosome is fused (2) thereto to form an autolysosome. Then, the selected molecule is degraded by a degrading enzyme. When not subjected to these degradation pathways, the selected molecule is released into cytoplasm or a nucleus (the dashed arrows in FIG. 1). Then, the selected molecule can exert a function of interest and can thus be utilized for research and/or practical use.

Specifically, to increase the efficiency of introducing a selected molecule, it seems useful to inhibit the above endocytosis pathway (A)- or autophagy pathway (B)-mediated lysosomal degradation to stabilize the selected molecule-containing vesicle and the selected molecule released from the vesicle into cytoplasm. Accordingly, an inhibitor used in the invention is an inhibitor of the above intracellular degradation pathway(s) and preferably an inhibitor of an endocytosis- or autophagy-mediated lysosomal degradation pathway.

It is preferable to use, as an inhibitor in the invention, an inhibitor of (1) maturation to a late endosome or (2) membrane fusion with a lysosome in the endocytosis-mediated lysosomal degradation pathway (A) or an inhibitor of (3) formation of an autophagosome or (2) membrane fusion with a lysosome in the autophagy-mediated lysosomal degradation pathway (B).

Examples of the inhibitor of (1) maturation from an early endosome to a late endosome include nocodazole or bafilomycin. Examples of the inhibitor of (2) membrane fusion with a lysosome include chloroquine or Lys05 that inhibits the activity of lysosome by making its acidic lysosome lumen alkaline. Examples of the inhibitor of (3) formation of an autophagosome include an inhibitor such as an inhibitor of PI3K, an enzyme that phosphorylates an inositol phospholipid. Examples of the PI3K inhibitor include LY-294002 (2-(4-morpholinyl)-8-phenyl-4H-1-benzopyran-4-one), wortmannin, or 3-methyladenine. In addition, examples of the inhibitor of autophagy include an inhibitor such as a protein synthesis inhibitor (e.g., cycloheximide), H(+)-ATPase inhibitor (e.g., bafilomycin A1), or an acidic protease inhibitor (e.g., leupeptin, E64d, pepstatin A).

It is preferable that an inhibitor in the invention is a low-molecular-weight compound permeable to a cell membrane by passive transport. The passive transport refers to concentration gradient-dependent transport without consuming energy. Examples thereof include simple diffusion or facilitated diffusion. Examples of the compound easily permeable to a cell membrane and functioning effectively include a compound with a molecular weight of 1000 or less. The concentration of the low-molecular-weight compound in a culture medium is preferably from 10 nM to 100 µM.

Preferably, a low-molecular-weight compound in the invention is at least one selected from the group consisting of nocodazole, chloroquine, LY-294002, and wortmannin.

The concentration of nocodazole in a culture medium contacted with a target cell, etc., during the inhibitor treatment step is preferably from 0.01 µM to 100 µM and more preferably from 0.1 µM to 10 µM.

The concentration of chloroquine in a culture medium contacted with a target cell, etc., during the inhibitor treatment step is preferably from 0.01 µM to 100 µM and more preferably from 1 µM to 100 µM.

The concentration of LY-294002 in a culture medium contacted with a target cell, etc., during the inhibitor treatment step is preferably from 0.01 µM to 100 µM and more preferably from 0.5 µM to 50 µM.

The concentration of wortmannin in a culture medium contacted with a target cell, etc., during the inhibitor treatment step is preferably from 0.001 µM to 0.1 µM and more preferably from 0.001 µM to 0.05 µM.

(Target Cell)

The target cell used in a method for introducing a selected molecule according to the invention refers to a target cell into which a selected molecule is introduced and is not limited to, in particular, a specific type of cell. Specific examples of such a target cell include a cell from animal including human, a cell collected from an individual organism body or tissue, a cell in an individual organism body or tissue, a plant cell, or a microbial cell. In addition, the cell may be an adherent cell or a floating cell. In the invention, selected molecules may be introduced simultaneously into a plurality of target cells. A single type of these target cells may be used, or two or more different types may be mixed and used.

Examples of the above cell collected from an individual organism body or tissue include: a cell that is not presumed to be returned to an individual organism body used for the R&D of a pharmaceutical agent, etc.; or a cell that is presumed to be returned to an individual organism body used for regenerative medicine, etc. In addition, examples of the above cell collected from an individual organism body or tissue include a cell cultured after collected from an individual organism body or tissue.

Here, in view of an aspect other than the above, examples of the target cell used in the invention include a prokaryotic cell from, for instance, *E. coli*, actinomycete, or *Bacillus subtilis*, or an eukaryotic cell such as yeast, an insect cell, a non-human animal cell, a cell collected from an individual human body, a cell included in an individual human body, or a plant cell. Examples of the non-human animal cell include, but are not particularly limited to, a cell derived from a mouse, a rat, a dog, a rabbit, a goat, or the like.

Furthermore, the target cell used in the invention may not be subjected to specific treatment and, in order to increase the efficiency of introducing a selected molecule, may be subjected to treatment to prepare a competent cell, which is commonly used at the time of gene introduction. Specific examples include an *E. coli* competent cell that is treated with calcium chloride so as to change the structure of a cell membrane, so that a DNA molecule is readily permeable thereto.

(Target Tissue)

Meanwhile, the target tissue used in the invention refers to a target tissue into which a selected molecule is introduced and is not limited to, in particular, a specific type of tissue. Specific examples of such a target tissue include: a donor-derived organ used for transplantation; a tissue such as the skin or a tooth root reconstructed using a procedure for regenerative medicine; or a pre-differentiation plant tissue constructed by callus culture. A single type of these target tissues may be used, or two or more different types may be mixed and used.

[Introduction Step]

In an introduction step in the invention, an introduction liquid containing a selected molecule is contacted with a target cell or a target tissue to introduce the selected molecule into the target cell or the target tissue.

(Selected Molecule)

The selected molecule used in a method for introducing a selected molecule into a target cell or a target tissue according to the invention refers to a molecule selected for introduction into a target cell, etc., and is not limited to a specific kind of molecule. Specific examples of such a selected molecule include a polymer compound such as DNA, RNA, or another nucleic acid molecule or a derivative thereof, or a protein or peptide, such as a signaling protein or a transcription regulatory factor, or a derivative thereof.

In addition, the above DNA or RNA may be a single strand or a double strand and may be linear or circular. Examples of the derivative of nucleic acid molecule include a vector, an antisense polynucleotide, a decoy polynucleotide, a ribozyme, or an siRNA. The molecular weight of the polynucleotide is not particularly limited.

Further, examples of the above protein molecule or protein molecule derivative include a signaling factor, a transcription regulatory factor, each enzyme, each receptor, an antibody or a Fab fragment of the antibody, a genome editing protein, or a protein medicine that cannot be given orally.

Examples of another selected molecule include a low-molecular-weight physiologically active substance or a drug candidate. Among them, a low-molecular-weight compound is preferable which is a physiologically active low-molecular-weight compound such as a pharmaceutical agent and is unlikely to be introduced into a tissue or a cell by other introduction methods. The low-molecular-weight compound that is unlikely to be introduced into a tissue or a cell by other introduction methods refers to a small molecule with a molecular weight of 1000 or higher, a molecule with low membrane permeability, or the like.

A single kind of the above-described respective selected molecules may be used, or two or more different kinds may be mixed and used.

(Introduction Liquid)

The introduction liquid containing a selected molecule is preferably suspended in a suitable medium such as water or an aqueous solution. Examples of a solvent or a dispersion medium for the aqueous solution or the suspension include saline or a pH buffer solution.

When the introduction liquid containing a selected molecule is contacted with a target cell, etc., it is possible to use, for instance, a procedure including dripping a liquid containing a selected molecule onto a target cell, etc., a procedure including mixing a target cell, etc., and a liquid containing a selected molecule, or the like. In addition, as another procedure, it is possible to use a procedure including adding a liquid containing a selected molecule to a dispersion liquid or a suspension containing a target cell, etc.

Further, in an introduction step in the invention, a selected molecule is preferably introduced via endocytosis into a target cell or a target tissue. This is because when a selected molecule is introduced via endocytosis into a target cell, etc., the pathway where an early endosome encapsulating the selected molecule occurs and the resulting early endosome undergoes a late endosome and is degraded in a lysosome is inhibited. In this way, the selected molecule can be stabilized.

In an introduction step in the invention, a selected molecule is preferably introduced by irradiating a target cell or a target tissue with plasma. The present inventors have conducted investigation and found that when plasma is used in the introduction step, a selected molecule is introduced into a cell via endocytosis using a vesicle. The method described in Japanese Patent Laying-Open No. 2013-255475 or Japanese Patent Laying-Open No. 2013-255474 may be used as a method for introducing a selected molecule by using plasma.

In the method for introducing a selected molecule by using plasma, it is possible to extend a plasma irradiation time and/or to raise a voltage so as to increase efficiency of introduction. However, cytotoxic effects are increased under such conditions. In the invention, a target cell, etc., may be treated with an inhibitor to keep stable an intracellular selected molecule. Thus, even if the plasma irradiation conditions are less restricted, it is possible to introduce the selected molecule highly efficiently. As a result, the cell viability can be enhanced. Such a plasma irradiation time is preferably a noticeably short period of from 0.1 msec to 5 msec.

In addition, the introduction liquid may contain a general-purpose transfection reagent utilizing endocytosis. In this case, plasma irradiation is not necessarily carried out in the step of introducing a selected molecule.

(Composition Containing Inhibitor)

A composition containing an inhibitor is used in the above method for introducing a selected molecule. The composition containing an inhibitor is not particularly limited as long as the liquid or solid (including a frozen liquid) can contain an inhibitor. Preferred is a liquid or solid that can stably contain an inhibitor. The composition containing an inhibitor may be, for instance, an aqueous solution (e.g., saline, a pH buffer solution) or a culture medium for a target cell, etc., or a target tissue containing an inhibitor, and preferably a culture medium for a target cell, etc., or a target tissue.

EXAMPLES

Hereinbelow, the invention will be described in more detail with reference to Examples. However, the invention is not limited to them.

Example 1

Mouse fibroblast L-929 cells were seeded on a 96-well plate and were cultured for 24 h in $CO_2$ incubator. A culture medium was removed by aspiration, and 100 μL of nocodazole (inhibitor) free-culture medium, 1 μM nocodazole-containing culture medium, or 100 μM nocodazole-containing culture medium was added to each well. The cells were cultured for 30 min in $CO_2$ incubator. Next, the culture medium was removed by aspiration, and 6.0 μg/6.0 μL of pAcGFP1-N1 plasmid (selected molecule) solution was added dropwise to each well. The 96-well plate was set in plasma irradiation equipment and irradiated with plasma. Then, 100 μL of culture medium was immediately added, and the plate was returned to $CO_2$ incubator and the cells were cultured for 24 h. The cells after the culturing were observed under a microscope.

Figure 2:
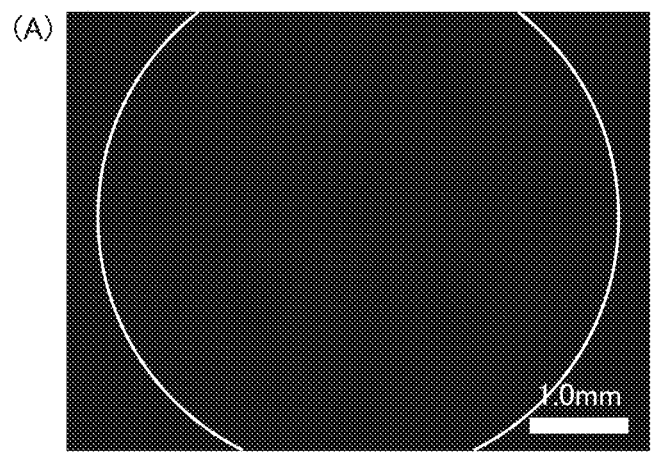
FIG. 2 shows (A) a captured fluorescent image of the whole one well on a 96-well plate, (B) a bright field image of a center portion of the well, and (C) a fluorescent image of the well center portion when GFP-expressing plasmid was introduced into L-929 cells without nocodazole treatment under plasma conditions for an irradiation time of 1 msec at a voltage of 15 kV.
Figure 2:
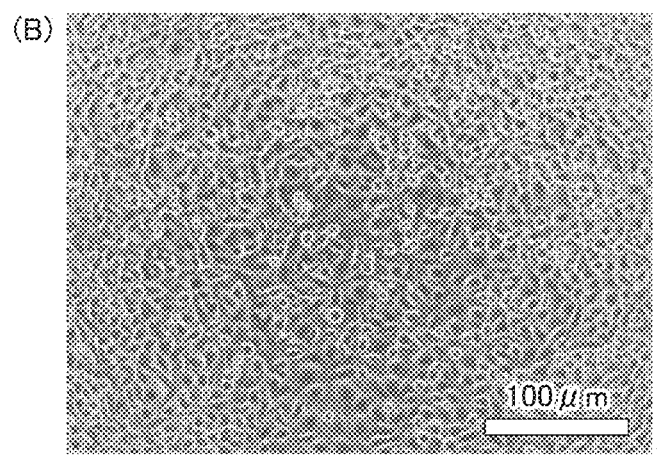
Figure 2:
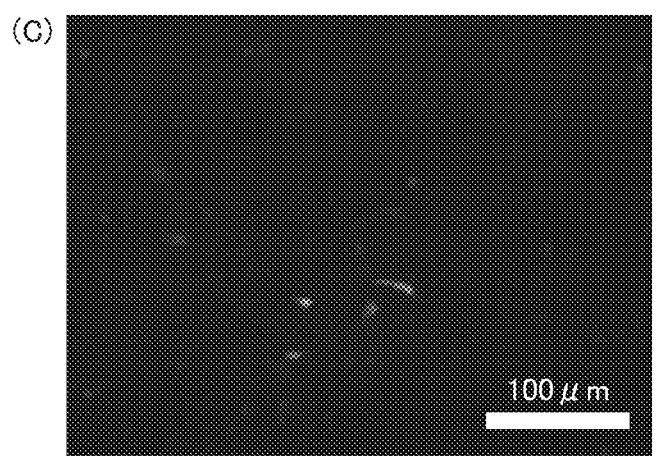
Figure 3:
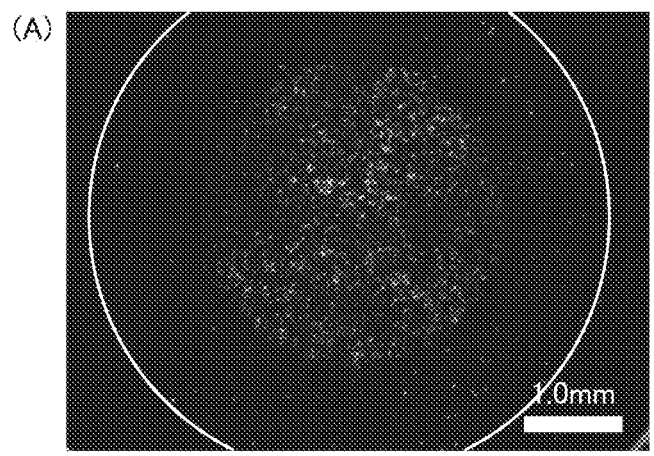
FIG. 3 shows (A) a captured fluorescent image of the whole one well on a 96-well plate, (B) a bright field image of a center portion of the well, and (C) a fluorescent image of the well center portion when GFP-expressing plasmid was introduced into L-929 cells with 1 µM nocodazole treatment under plasma conditions for an irradiation time of 1 msec at a voltage of 15 kV.
Figure 3:
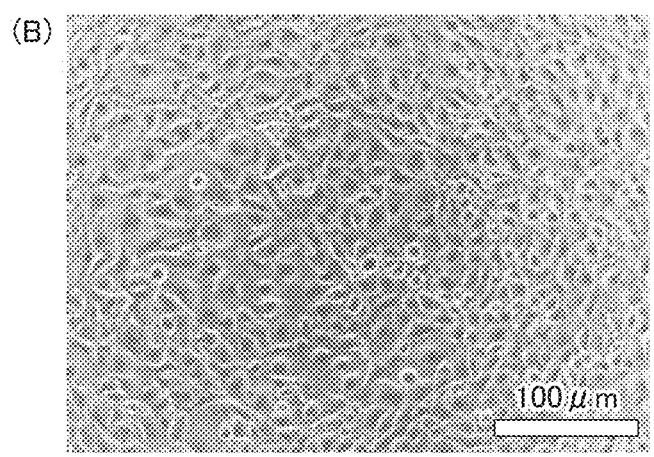
Figure 3:
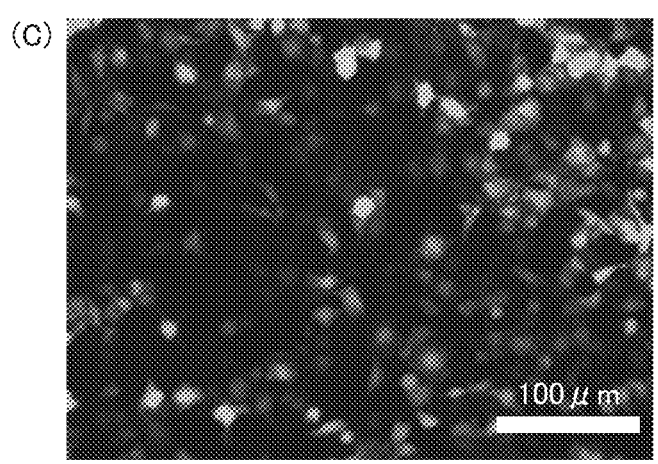
Figure 4:
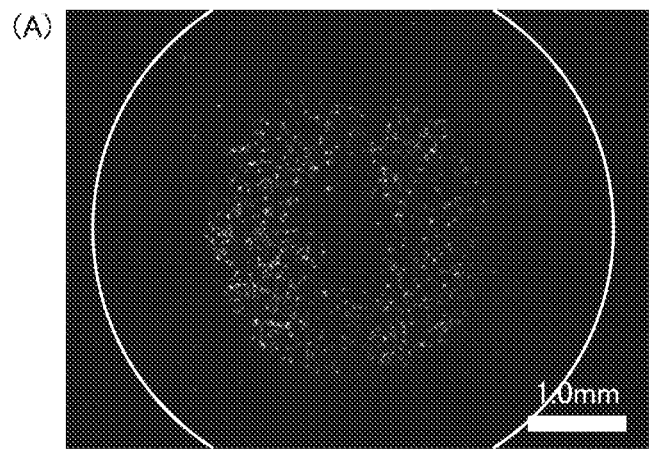
FIG. 4 shows (A) a captured fluorescent image of the whole one well on a 96-well plate, (B) a bright field image of a center portion of the well, and (C) a fluorescent image of the well center portion when GFP-expressing plasmid was introduced into L-929 cells with 100 µM nocodazole treatment under plasma conditions for an irradiation time of 5 msec at a voltage of 15 kV.
Figure 4:
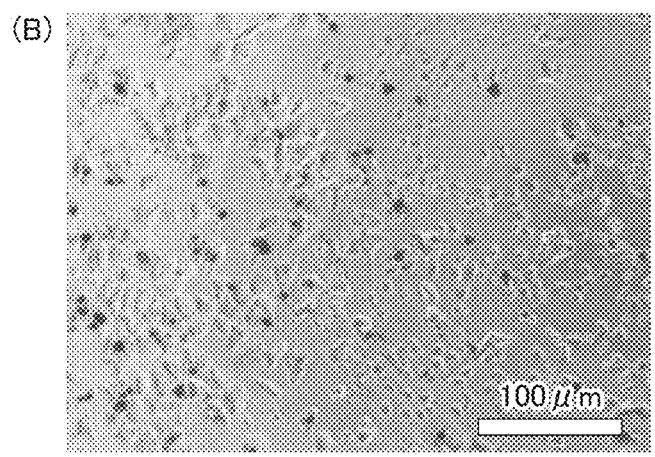
Figure 4:
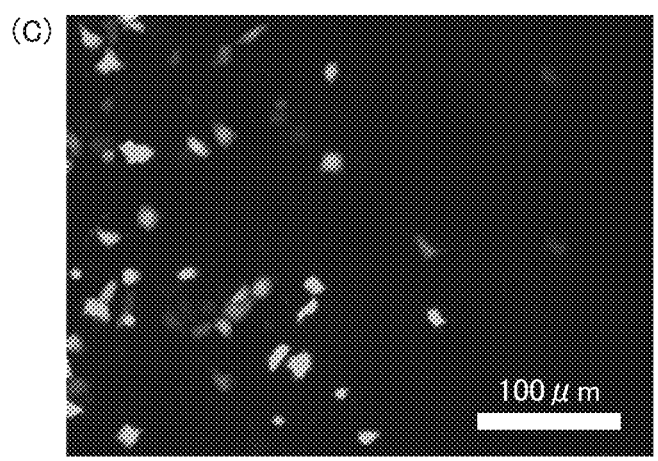

FIG. 2 shows (A) a captured fluorescent image of the whole one well on a 96-well plate, (B) a bright field image of a center portion of the well, and (C) a fluorescent image of the well center portion in the case without nocodazole treatment. FIG. 3 shows (A) a captured fluorescent image of the whole one well on a 96-well plate, (B) a bright field image of a center portion of the well, and (C) a fluorescent image of the well center portion in the case of 1 μM nocodazole treatment. FIG. 4 shows (A) a captured fluorescent image of the whole one well on a 96-well plate, (B) a bright field image of a center portion of the well, and (C) a fluorescent image of the well center portion in the case of 100 μM nocodazole treatment.

In Example 1, the plasma irradiation conditions were at a frequency of 20 kHz, a voltage of 15 kVpp, and an inter-electrode distance of 1 mm and for an irradiation time of 1 msec or 5 msec.

Example 2

Figure 5:
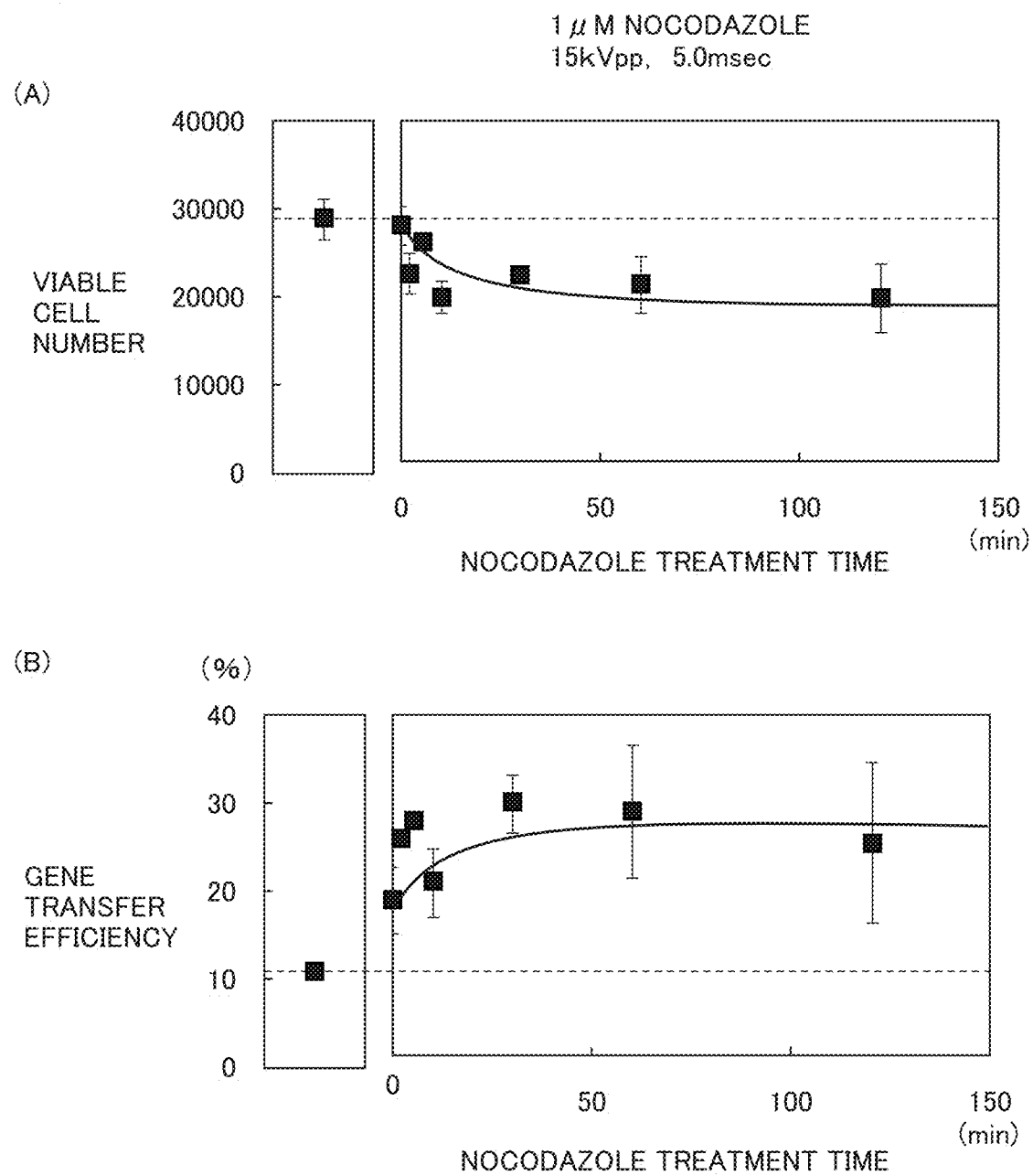
FIG. 5 is graphs showing (A) a viable cell number and (B) gene transfer efficiency when GFP-expressing plasmid was introduced into cells under conditions for a plasma irradiation time of 5 msec while the nocodazole (1 µM) treatment time was changed.
Figure 6:
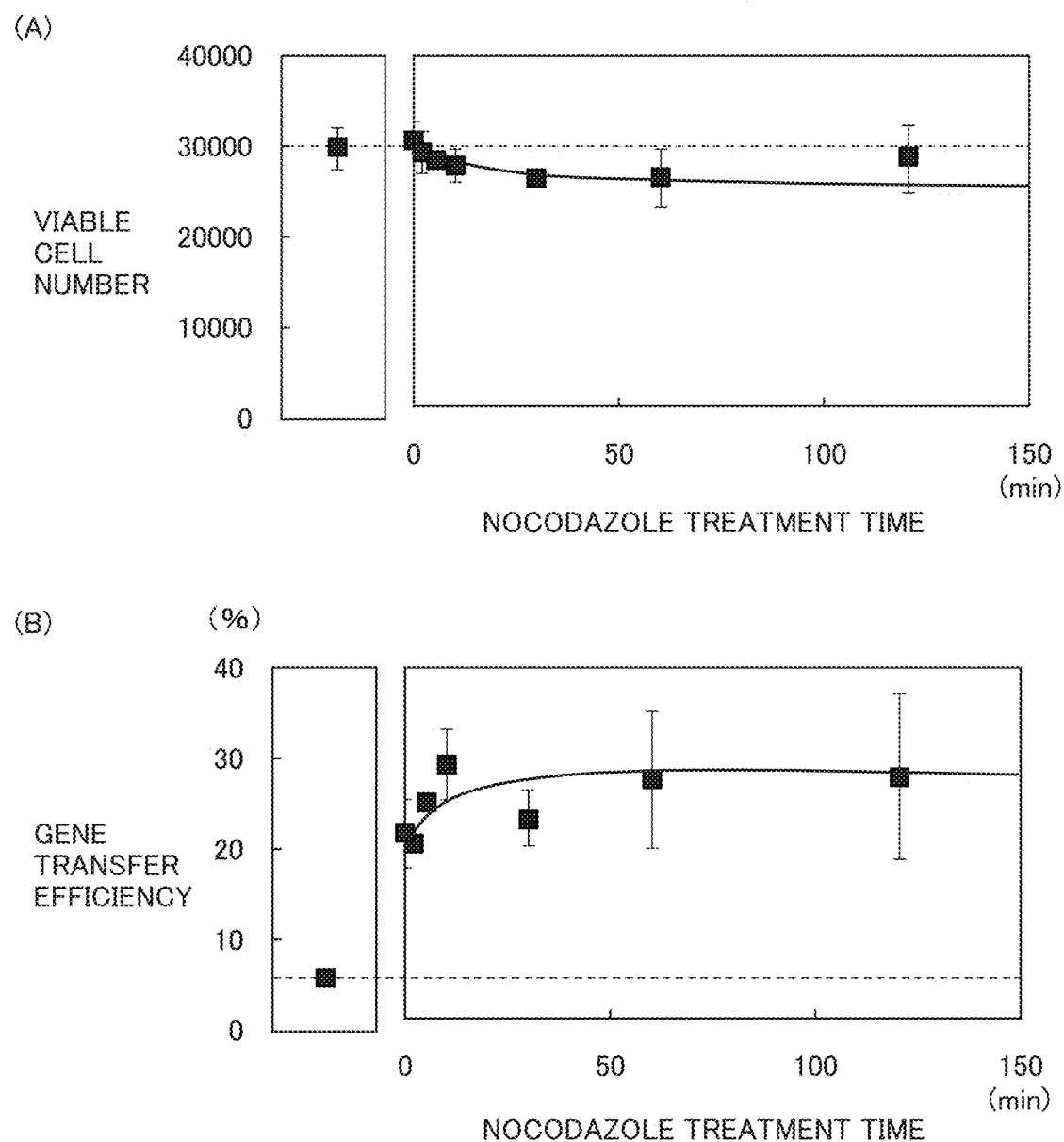
FIG. 6 is graphs showing (A) a viable cell number and (B) gene transfer efficiency when GFP-expressing plasmid was introduced into cells under conditions for a plasma irradiation time of 1 msec while the nocodazole (1 µM) treatment time was changed.

A selected molecule was introduced in the same manner as in Example 1, except the point that in the inhibitor treatment step using 1 μM nocodazole, the treatment time was changed from 1 min to 120 min. FIG. 5 shows (A) a viable cell number and (B) gene transfer efficiency when GFP-expressing plasmid was introduced into cells under conditions for a plasma irradiation time of 5 msec. FIG. 6 shows (A) a viable cell number and (B) gene transfer efficiency when GFP-expressing plasmid was introduced into cells under conditions for a plasma irradiation time of 1 msec. The dashed line denotes the level in the case without adding nocodazole (control, left panel). The gene transfer efficiency (%) was calculated, using a Cytell (Cytell Cell Imaging System, manufactured by GE Healthcare, Inc.), as (the number of GFP-expressing cells/viable cell number).

Example 3

Figure 7:
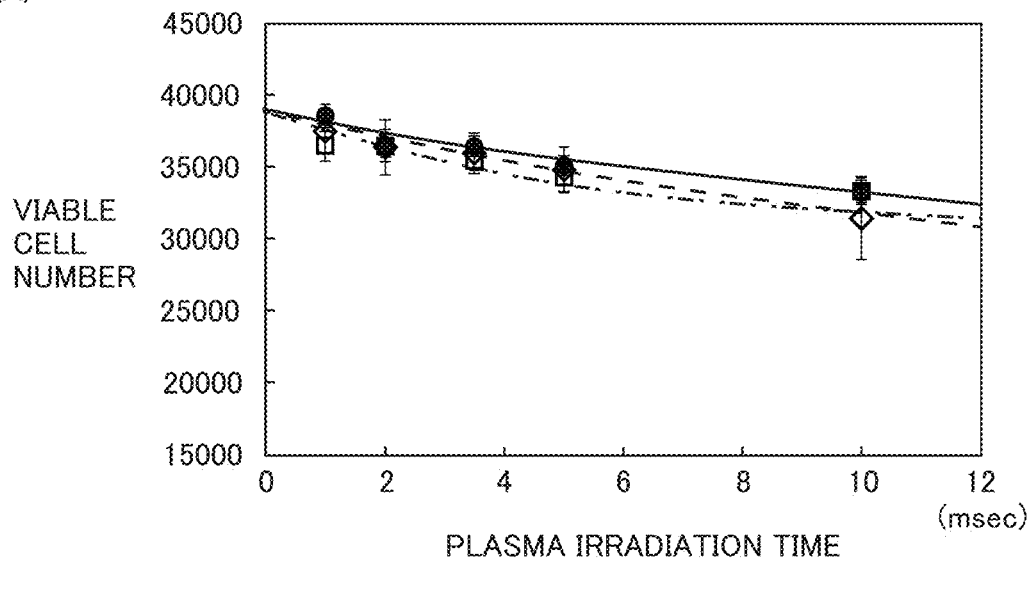
FIG. 7 is graphs showing (A) a viable cell number and (B) gene transfer efficiency when cells were treated with chloroquine-free culture medium (std), 5 µM chloroquine-containing culture medium (5 µM), or 15 µM chloroquine-containing culture medium (15 µM) while the plasma irradiation time was changed from 1 msec to 10 msec.
Figure 7:
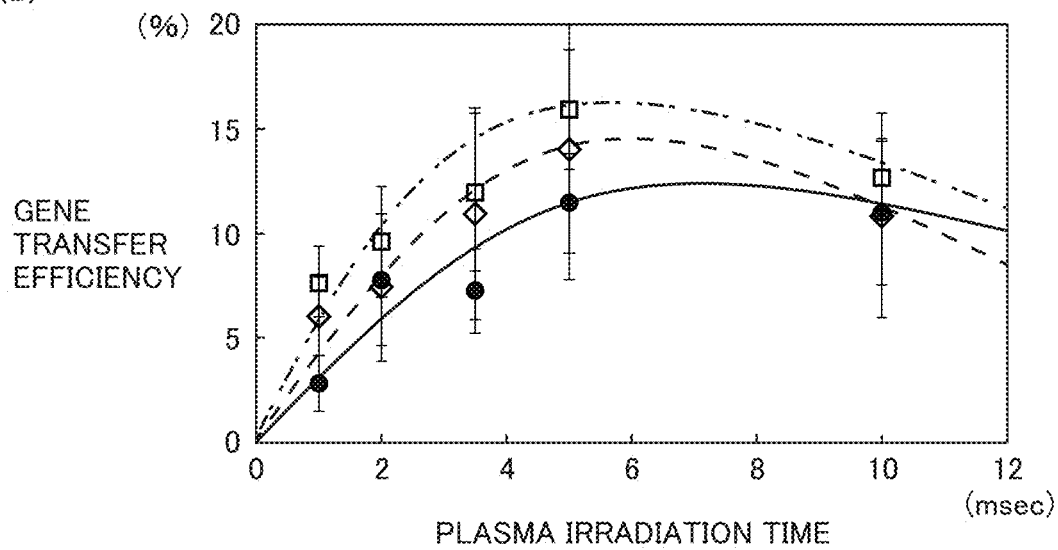

A selected molecule was introduced in the same manner as in Example 1, except the point that the cells were treated with 5 μM or 15 μM chloroquine diphosphate and the plasma irradiation time was changed. FIG. 7 shows (A) a viable cell number and (B) gene transfer efficiency when cells were treated with chloroquine-free culture medium (std), 5 μM chloroquine-containing culture medium (5 μM), or 15 μM chloroquine-containing culture medium (15 μM) while the plasma irradiation time was changed from 1 msec to 10 msec.

Example 4

Figure 8:
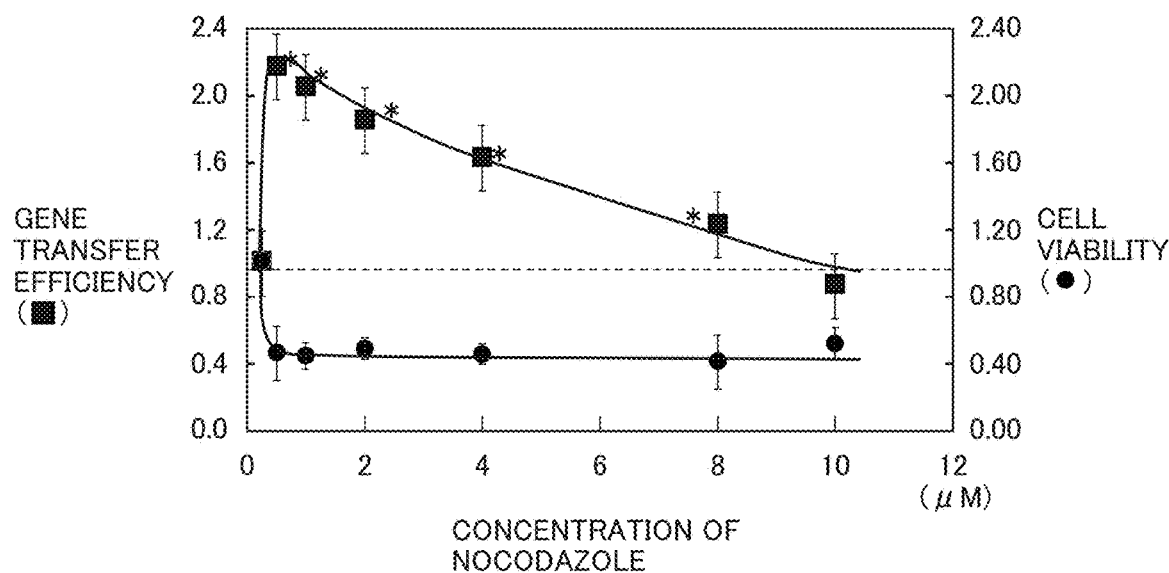
FIG. 8 is a graph showing normalized cell viability and gene transfer efficiency while the concentration of nocodazole was changed.

A selected molecule was introduced in the same manner as in Example 1, except the point that the concentration of nocodazole was changed, to determine cell viability and gene transfer efficiency. The plasma irradiation conditions were at a frequency of 20 kHz, a voltage of 15 kVpp, and an inter-electrode distance of 1 mm and for an irradiation time of 1 msec. FIG. 8 shows the results normalized while the level in the (control) case without adding nocodazole was set to 1. The dashed line denotes the control (P<0.05). In the following Examples 5 to 7, the level indicated was likewise normalized.

Example 5

Figure 9:
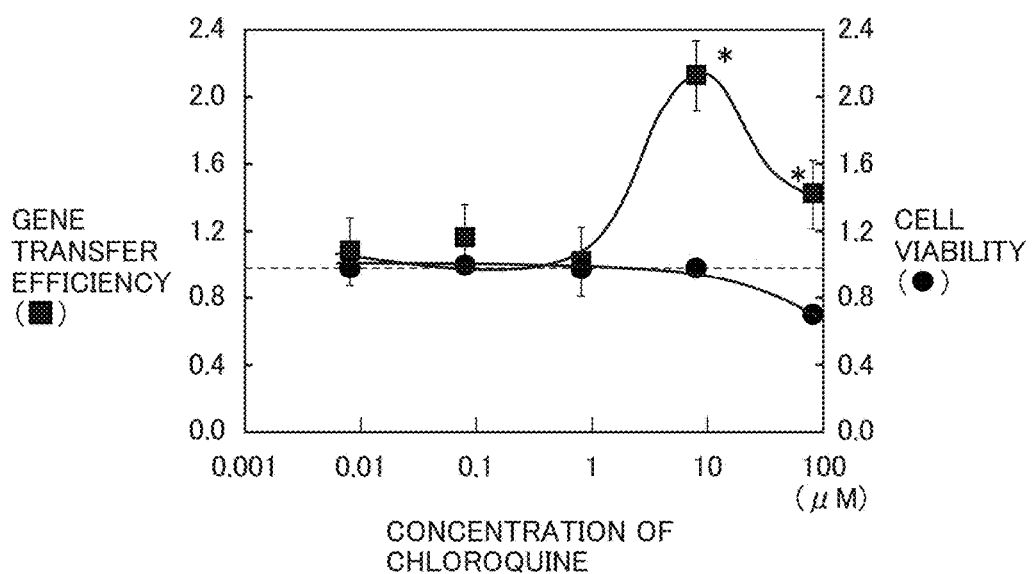
FIG. 9 is a graph showing normalized cell viability and gene transfer efficiency while the concentration of chloroquine was changed.

Cell viability and gene transfer efficiency were determined in the same manner as in Example 4, except the point that chloroquine was used as the inhibitor. FIG. 9 shows the results.

Example 6

Figure 10:
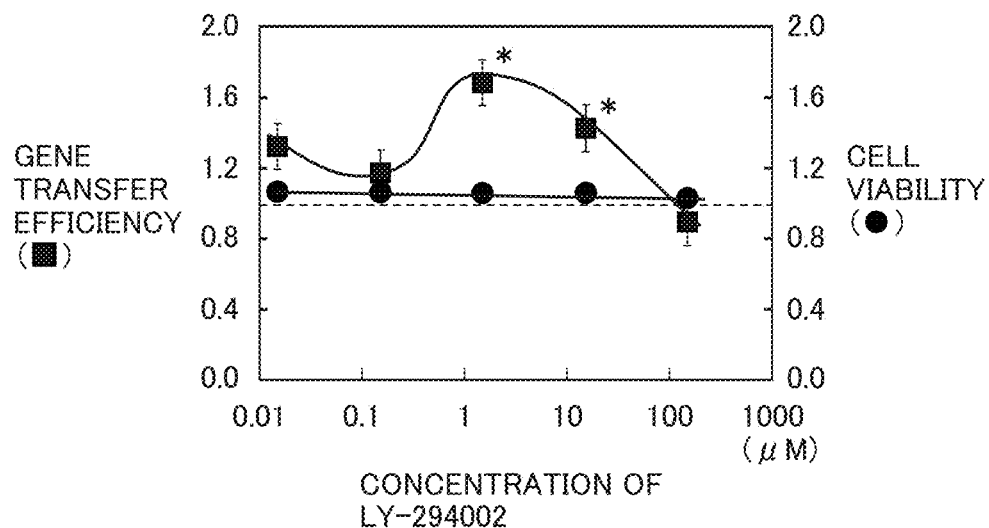
FIG. 10 is a graph showing normalized cell viability and gene transfer efficiency while the concentration of LY-294002 was changed.

Cell viability and gene transfer efficiency were determined in the same manner as in Example 4, except the point that LY-294002 was used as the inhibitor. FIG. 10 shows the results.

Example 7

Figure 11:
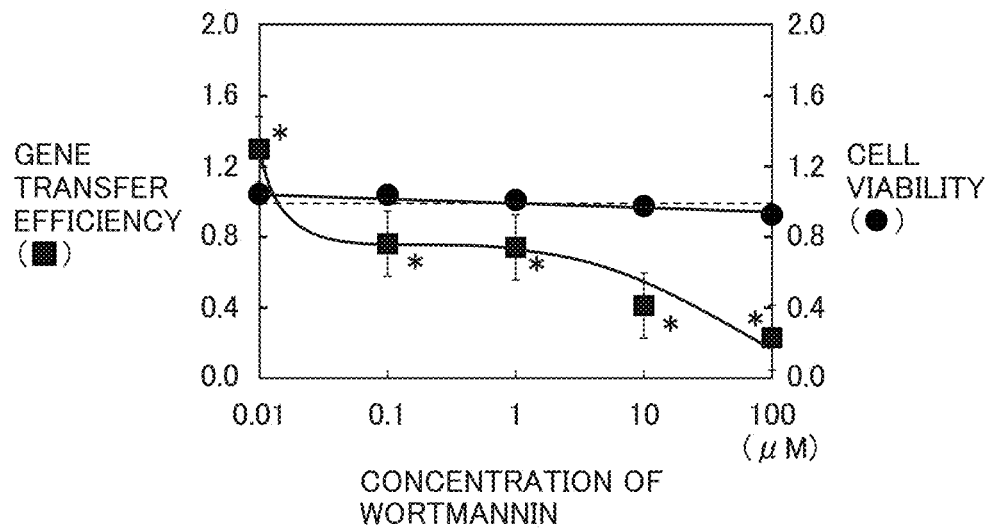
FIG. 11 is a graph showing normalized cell viability and gene transfer efficiency while the concentration of wortmannin was changed.

Cell viability and gene transfer efficiency were determined in the same manner as in Example 4, except the point that wortmannin was used as the inhibitor. FIG. 11 shows the results.

Example 8

An experiment was conducted in the same manner as in Experiment 1, except that cells (human osteosarcoma cells, MG63 cells) different from those in Example 1 were used. The concentration of nocodazole was 1 µM or 0.1 µM.

Figure 12:
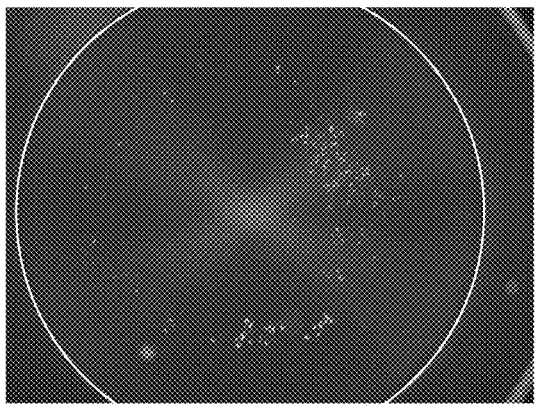
FIG. 12 is images showing gene expression when the concentration of nocodazole was changed while MG63 cells (human osteosarcoma cells) were used. The images shown are (A) a fluorescent image and (B) a bright field image when cells were not treated with nocodazole, (C) a fluorescent image and (D) a bright field image when cells were treated with 1.0 µM nocodazole, and (E) a fluorescent image and (F) a bright field image when cells were treated with 0.1 µM nocodazole.
Figure 12:
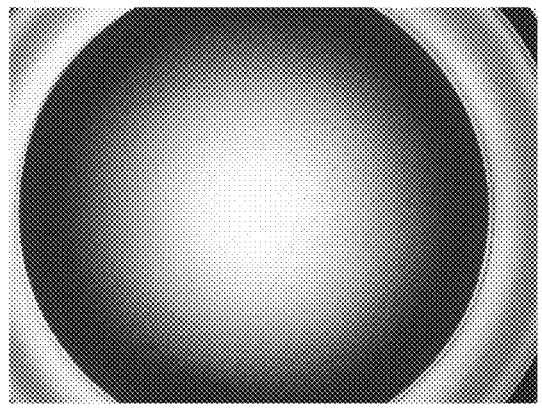
Figure 12:
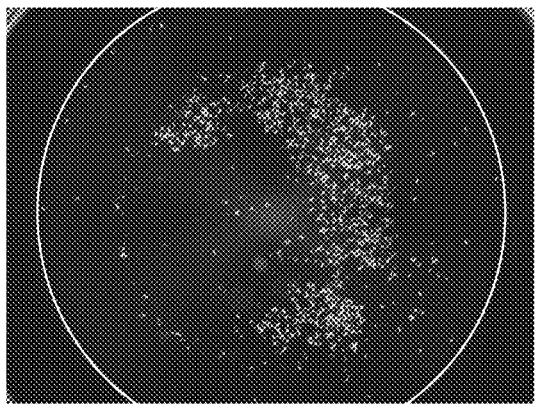
Figure 12:
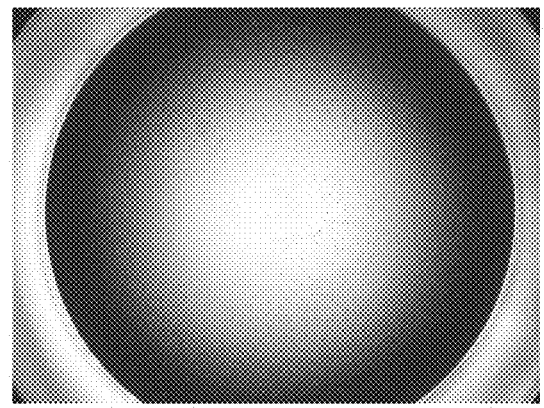
Figure 12:
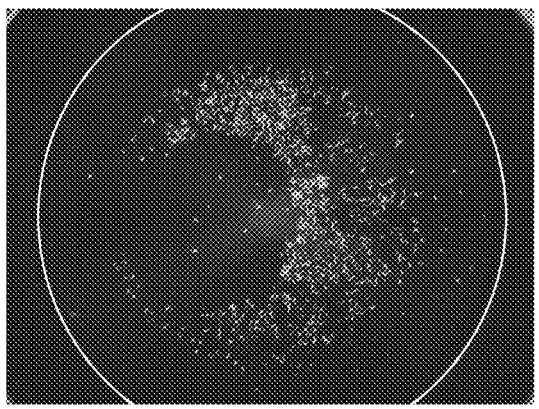
Figure 12:
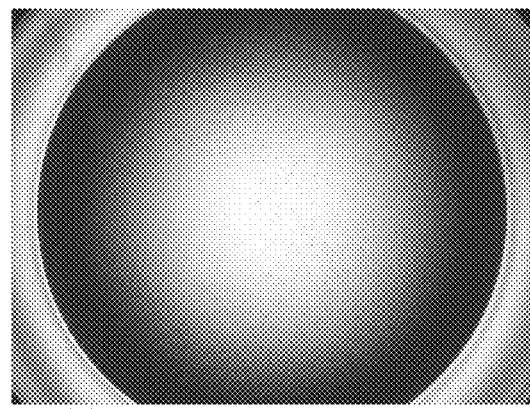

FIG. 12 shows (A) a captured fluorescent image of the whole one well on a 96-well plate and (B) a bright field image of the whole one well in the case without nocodazole treatment. In addition, it shows (C) a captured fluorescent image of the whole one well on a 96-well plate and (D) a bright field image of the whole one well in the case of 1 µM nocodazole treatment. Further, it shows (E) a captured fluorescent image of the whole one well on a 96-well plate and (F) a bright field image of the whole one well in the case of 0.1 µM nocodazole treatment.

Example 9

By using cells (canine renal epithelial cell MDCK cells or human osteosarcoma cell MG63 cells) different from those in Example 1, gene transfer efficiency was examined when nocodazole treatment was performed after plasma irradiation. Specifically, the following protocol was used to conduct an experiment.

Canine renal epithelial cell MDCK cells or human osteosarcoma cell MG63 cells were each seeded on a 96-well plate and cultured for 24 h in $CO_2$ incubator. The culture medium was removed by aspiration, and 6.0 µg/6.0 µL of pAcGFP1-N1 plasmid (selected molecule) solution was added dropwise to each well. The 96-well plate was set in plasma irradiation equipment and was irradiated with plasma. Then, 100 µL of nocodazole (inhibitor)-free culture medium, 1 µM nocodazole-containing culture medium, or 0.1 µM nocodazole-containing culture medium was added to each well. The cells were cultured for 30 min in $CO_2$ incubator. After that, the culture medium was removed by aspiration and 100 µL of culture medium was added immediately. The plate was returned to $CO_2$ incubator, and the cells were cultured for 24 h. The cells after the culturing were observed under a microscope. The plasma irradiation conditions were the same as in Example 1.

Figure 13:
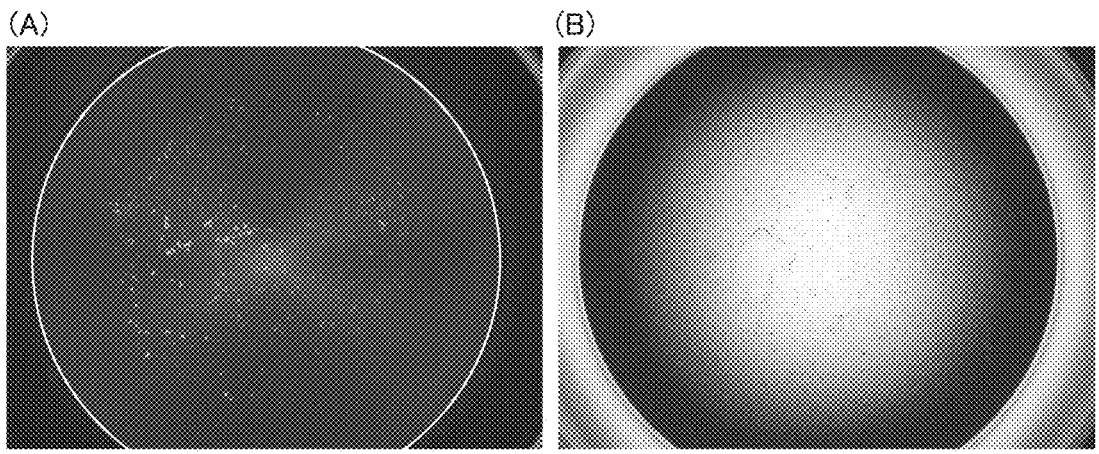
FIG. 13 is images showing gene expression when MDCK cells (canine renal epithelial cells) were treated with nocodazole after plasma irradiation. The images shown are (A) a fluorescent image and (B) a bright field image when cells were not treated with nocodazole, (C) a fluorescent image and (D) a bright field image when cells were treated with 1.0 µM nocodazole, and (E) a fluorescent image and (F) a bright field image when cells were treated with 0.1 µM nocodazole.
Figure 13:
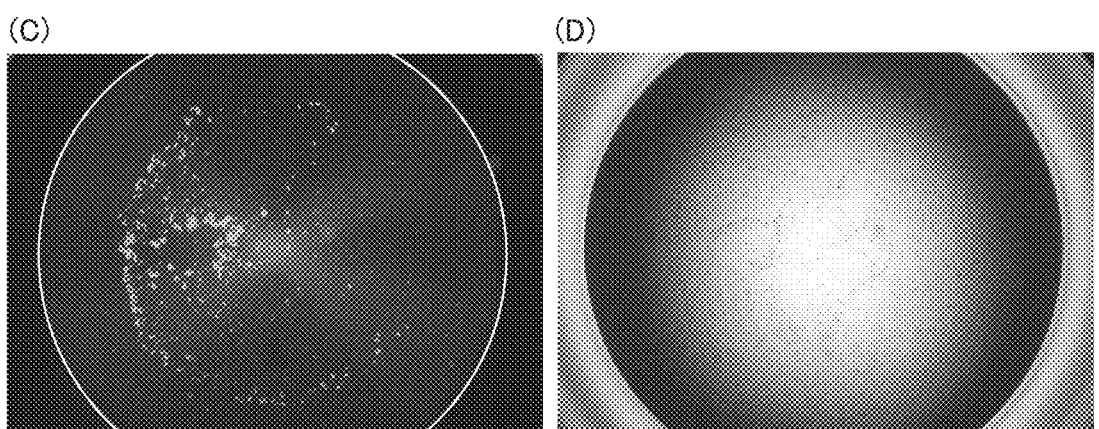
Figure 13:
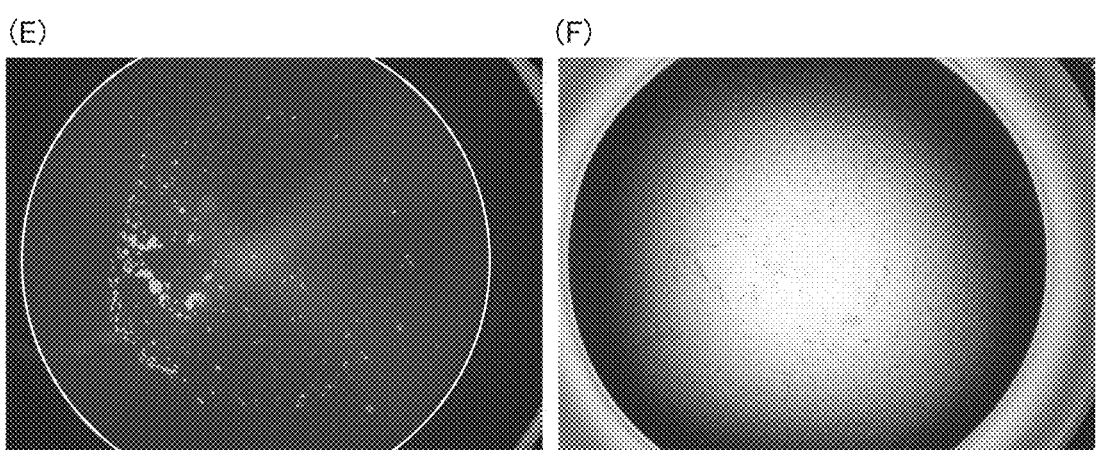
Figure 14:
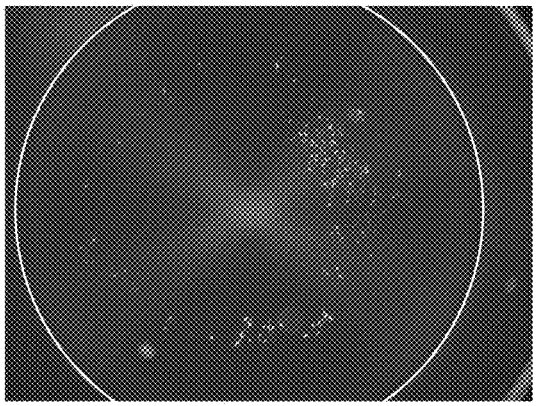
FIG. 14 is images showing gene expression when MG63 cells (human osteosarcoma cells) were treated with nocodazole after plasma irradiation. The images shown are (A) a fluorescent image and (B) a bright field image when cells were not treated with nocodazole, (C) a fluorescent image and (D) a bright field image when cells were treated with 1.0 µM nocodazole, and (E) a fluorescent image and (F) a bright field image when cells were treated with 0.1 µM nocodazole.
Figure 14:
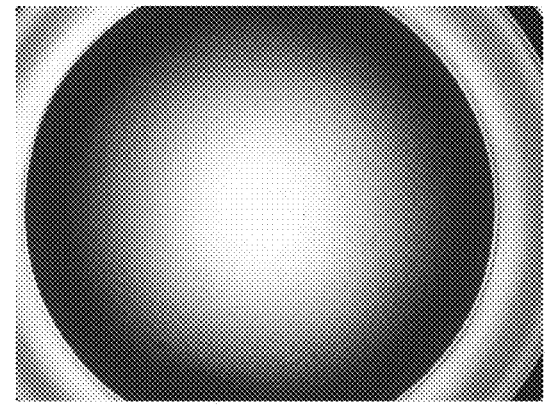
Figure 14:
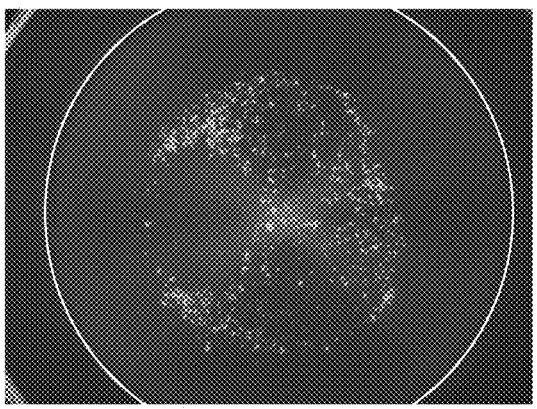
Figure 14:
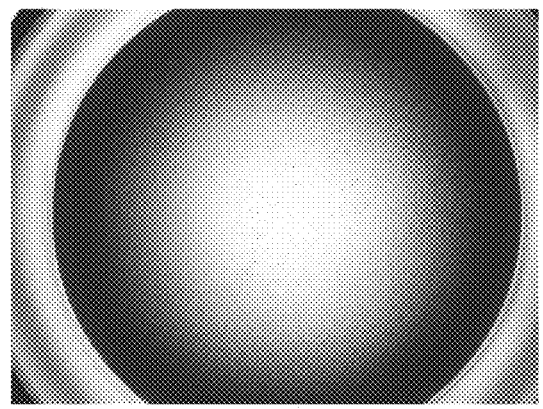
Figure 14:
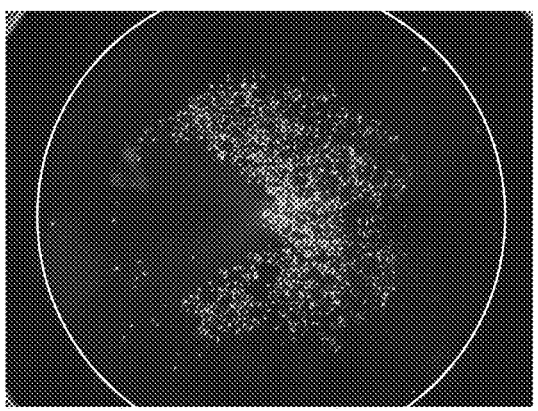
Figure 14:
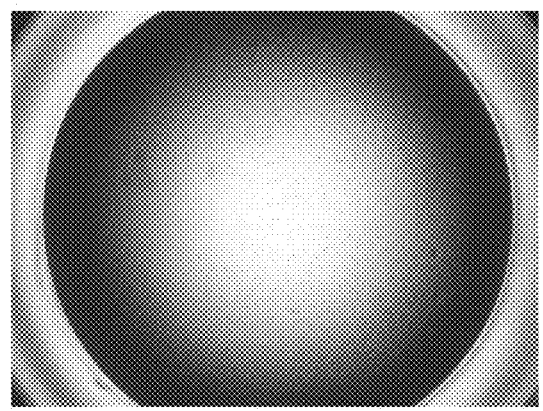

(A) A captured fluorescent image of the whole one well on a 96-well plate and (B) a bright field image of the whole one well in the case without nocodazole treatment are shown in FIG. 13 for MDCK cells and in FIG. 14 for MG63 cells, respectively. In addition, (C) a captured fluorescent image of the whole one well on a 96-well plate and (D) a bright field image of the whole one well in the case of 1 µM nocodazole treatment are shown. Further, (E) a captured fluorescent image of the whole one well on a 96-well plate and (F) a bright field image of the whole one well in the case of 0.1 µM nocodazole treatment are shown.

Example 10

How nocodazole (inhibitor) treatment caused a change in the level of intracellular exogenous gene was investigated. A selected molecule was introduced into mouse fibroblast L-929 cells in the same procedure as in Example 1. The resulting cells were cultured for 24 h. The concentration of nocodazole was 1 µM. The cultured cells were collected from eight wells, and a High Pure PCR Template Preparation Kit (manufactured by Roche, Inc.) was used to recover and purify DNA. Next, 50 ng of the purified DNA was added to a PCR reaction kit SYBR Green I (Fast Start Essential DNA Green Master, manufactured by Roche, Inc.). Each resulting mixture was subjected to 40 cycles of amplification using a PCR machine (LightCycler 96 system, manufactured by Roche, Inc.). The sequences of two primers pAcGFP1-N1-For and pAcGFP1-N1-Rev used for the GFP gene amplification are as follows.

```
pAcGFP1-N1-For:
ATAGCGGTTTGACTCACGGG;
and pAcGFP1-N1-Rev:
GATCGGGGTAGCGTGAGAAG.
```

Figure 15:
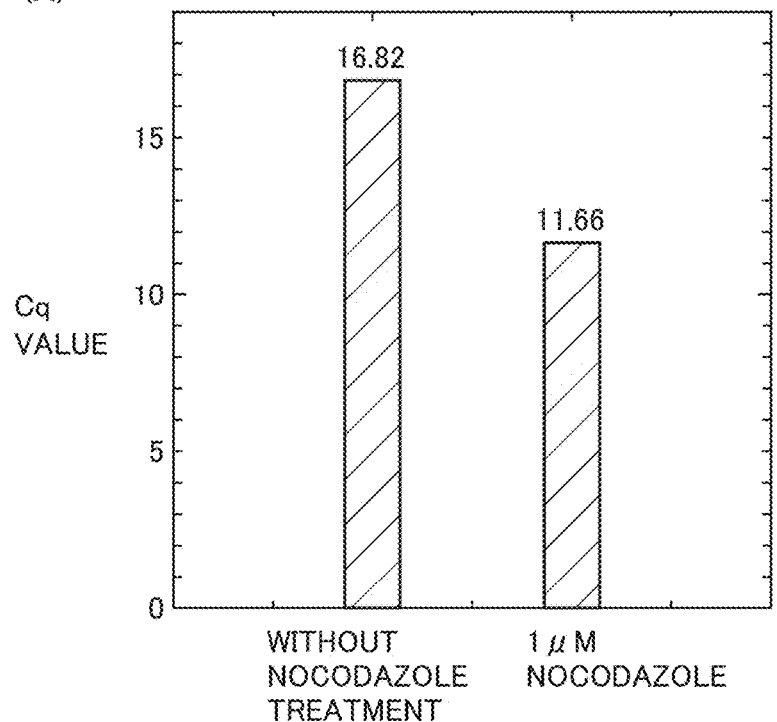
FIG. 15 is graphs showing (A) Cq values and (B) gene amplification curves when the remaining level of selected molecule (plasmid gene) at 24 h after introduction was quantified by PCR in cells without nocodazole treatment or cells with 1 µM nocodazole treatment.
Figure 15:
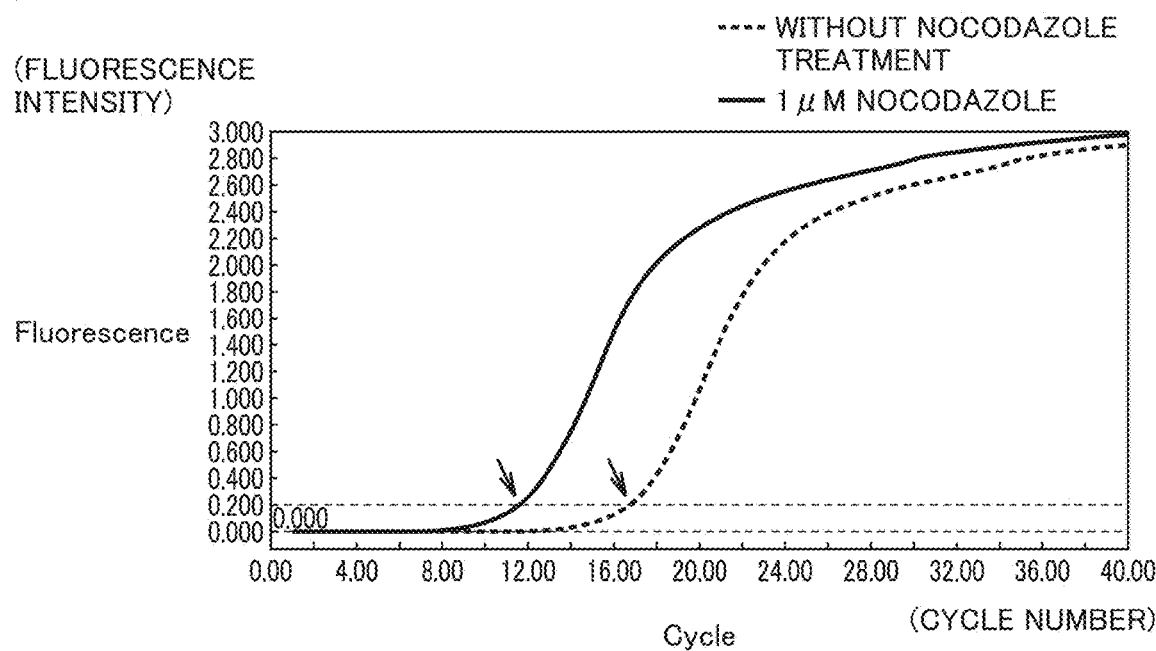

FIG. 15 shows Cq values and gene amplification curves obtained by a PCR method. Each Cq value refers to a value determined by calculating a cycle number after amplification of gene sequence of interest has started and before a quantitative increase (linear increase) is initiated. The cycle number indicated by each arrow in FIG. 15(B) refers to the Cq value. When many copies of the gene sequence of interest are contained, there is a rapid increase in amplification and the Cq value is small. In addition, the inverse number of Cq value is proportional to the initial amount of the gene sequence of interest.

<Results>

As shown in FIGS. 2 to 4, in the case of 1 µM or 100 µM nocodazole treatment at the time of gene introduction, the number of GFP-expressing cells was increased when compared to the case without nocodazole treatment. Under conditions without any inhibitor, the gene transfer efficiency in the case of plasma irradiation for a short time of 1 msec was low. However, the inhibitor treatment successfully caused the gene transfer efficiency and expression efficiency to increase. In addition, this result has demonstrated that even regarding cells that have conventionally determined to have no observed GFP expression and be impossible to have a gene introduced, the gene was actually introduced in the cells as seen in FIG. 2, suggesting that majority of the gene molecules were degraded.

Likewise, as shown in FIG. 5(B), the gene transfer efficiency was markedly increased in the cells with (1 µM) nocodazole treatment when compared to the cells without nocodazole treatment (dashed line). In addition, the results of FIG. 6(B) have also demonstrated a marked increase in the gene transfer efficiency after nocodazole treatment. From this result, the nocodazole treatment time may be preferably 1 min or longer and more preferably 10 min or longer.

Further, under conditions at a nocodazole concentration of 1 μM, the cytotoxic effects were alleviated more in the case of plasma irradiation time of 1 msec than the case of irradiation time of 5 msec (FIG. 5(A) and FIG. 6(A)) while the gene transfer efficiency remained the same (FIG. 5(B) and FIG. 6(B)).

Conventionally, strong plasma irradiation was required so as to introduce a sufficient amount of selected molecule to exert its function. Unfortunately, a longer plasma irradiation time and/or a stronger voltage applied caused cell damage. Thus, it has been difficult to establish both high transfer efficiency and cell viability. According to the invention, nocodazole treatment causes suppression of degradation of selected molecule introduced into a cell. Consequently, the selected molecule can be stabilized under weak plasma irradiation conditions and can be intracellularly maintained at a high concentration. Hence, cell death can be prevented, so that it is possible to obtain a large number of cells that can highly efficiently elicit a function of the selected molecule.

Likewise, as shown in FIG. 7(B), the gene transfer efficiency was increased in the cells treated with a culture medium having a chloroquine concentration of 5 μM or 15 μM and irradiated with plasma when compared to the cells without chloroquine treatment (std). That is, in the case of chloroquine treatment, even a shorter plasma irradiation time can cause substantially the same gene transfer efficiency as in the case of longer irradiation. As shown in FIG. 7(A), a longer plasma irradiation time causes higher cytotoxic effects, which decrease cell viability. Accordingly, the chloroquine treatment with short plasma irradiation makes it possible to keep the efficiency of introducing a selected molecule, thereby increasing cell viability. Because of this, it is possible to obtain a larger number of cells having the selected molecule introduced. This can elevate the gene transfer efficiency after the cell viability is taken into account.

The results of FIGS. 8 to 11 have demonstrated that in the case of treating cells with nocodazole or chloroquine, or even LY-294002 or wortmannin, the gene introduction rate was significantly increased when compared to the case without each treatment. The gene transfer efficiency was further markedly increased in the case of nocodazole concentration of from 0.1 μM to 10 μM shown in FIG. 8, in the case of chloroquine concentration of from 1 μM to 100 μM shown in FIG. 9, in the case of LY-294002 concentration of from 0.5 μM to 50 μM shown in FIG. 10, and with low-concentration treatment at a wortmannin concentration of 0.01 μM or lower shown in FIG. 11. It has been found that these inhibitors, which have each been known as a compound that inhibits an endocytosis- or autophagy-mediated lysosomal degradation, can increase the efficiency of introducing a selected molecule via endocytosis.

As shown in FIG. 12, when a gene was introduced into human fibroblasts while treated with 1.0 μM or 0.1 μM nocodazole, the number of GFP-expressing cells was increased more than in the case without nocodazole treatment. In addition, as shown in FIG. 13, when a gene was introduced into dog-derived cells while treated with 1.0 μM or 0.1 μM nocodazole, the number of GFP-expressing cells was increased more than in the case without nocodazole treatment. Thus, in the case of treatment with each compound, such as nocodazole, that inhibits an intracellular degradation mechanism, the gene expression efficiency was found to significantly increase regardless of the type of cells when compared to the case without each compound treatment.

Further, as shown in FIGS. 13 and 14, even in the case of performing nocodazole treatment after the gene introduction step, an increase in the number of GFP-expressing cells was observed when compared to the case without nocodazole treatment. The inhibitor treatment step performed before or even after the introduction step was found to be able to increase the efficiency of introducing a selected molecule.

FIG. 15 has demonstrated that the amount of exogenous gene DNA remaining in cells treated with nocodazole was about 1.44 times larger than the amount of DNA remaining in cells without nocodazole treatment. The results of Examples 1 to 9 (FIGS. 2 to 14) have demonstrated that the inhibitor treatment caused an increase in expression of a gene (selected molecule) introduced. The results of FIG. 15 have revealed that the above increase in the gene expression was due to a significant increase in the level of the introduced gene present in the cells after treated with an inhibitor such as nocodazole. The inhibitor of an endocytosis- or autophagy-mediated lysosomal degradation pathway functions to stabilize a selected molecule taken up into a cell by the introduction step. It has been revealed that the inhibitor can suppress a pathway leading to degradation of a selected molecule-containing vesicle itself and degradation of a selected molecule released from the vesicle. Accordingly, the selected molecule can be introduced when the number of selected molecules is made smaller or even when the plasma irradiation conditions are weaker. On top of that, it has been proved that a selected molecule can be introduced into each cell into which the selected molecule has previously been hardly introduced.

The embodiments and Examples disclosed herein are examples regarding every point and should not be considered to be limited. The scope of the invention is defined by the CLAIMS but not the above description. Any modifications within the scope and the equivalent meaning of the CLAIMS are intended to be included.

INDUSTRIAL APPLICABILITY

The invention makes it possible to introduce a selected molecule into each cell into which the selected molecule has previously been hardly introduced and also makes it possible to obtain a large number of cells expressing an exogenous gene or a protein at a high level. This allows for research on analyzing an in vivo function of specific molecule and application to broad fields including medicine, agriculture, and environment. Examples of the medical field include cell medicine, regenerative medicine, and gene therapy. In the agricultural field and environmental field, the invention is applicable to breed and selective breeding.

The invention claimed is:

1. A method for introducing a molecule, comprising:
   allowing a target cell or a target tissue to internalizing an inhibitor of an endocytosis- or autophagy-mediated lysosomal degradation pathway; and
   contacting a liquid containing a molecule with the target cell or the target tissue to introduce the molecule into the target cell or the target tissue.

2. The introduction method according to claim 1, wherein in the contacting, the molecule is introduced via endocytosis into the target cell or the target tissue.

3. The introduction method according to claim 1, wherein in the contacting, the molecule is introduced by irradiating the target cell or the target tissue with plasma.

4. The introduction method according to claim 1, wherein the inhibitor comprises a low-molecular-weight compound permeable to a cell membrane of the target cell or a cell as a component of the target tissue.

5. The introduction method according to claim 4, wherein the low-molecular-weight compound comprises at least one selected from the group consisting of nocodazole, chloroquine, LY-294002, and wortmannin.

6. The introduction method according to claim 1, wherein in the allowing, the target cell or the target tissue is allowed to internalize the inhibitor by contacting a composition containing the inhibitor with the target cell or the target tissue.

7. The introduction method according to claim 6, wherein the composition is a culture medium for the target cell or the target tissue.

8. The introduction method according to claim 1, wherein the molecule comprises a nucleic acid molecule, protein or peptide.

9. The introduction method according to claim 1, wherein the molecule comprises DNA or RNA.

10. The introduction method according to claim 1, wherein the molecule comprises a plasmid.

11. The introduction method according to claim 1, wherein the inhibitor comprises at least one selected from the group consisting of nocodazole, bafilomycin, chloroquine, Lys05, LY-294002 (2-(4-morpholinyl)-8-phenyl-4H-1-benzopyran-4-one), wortmannin, 3-methyladenine, cycloheximide, bafilomycin A1, leupeptin, E64d, and pepstatin A.

12. The introduction method according to claim 1, wherein the introduction liquid comprises water or aqueous solution.

13. The introduction method according to claim 1, wherein the target cell or target tissue comprises a plurality of target cells.

14. The introduction method according to claim 1, wherein the target cell or target tissue comprises a prokaryotic cell.

15. The introduction method according to claim 1, wherein the target cell or target tissue comprises a eukaryotic cell.

16. The introduction method according to claim 1, wherein the target cell or target tissue comprises a cell from a mouse, a rat, a dog, a rabbit, or a goat.

17. The introduction method according to claim 1, wherein the target cell or target tissue comprises a donor-derived organ used for transplantation or a pre-differentiation plant tissue constructed by callus culture.

\* \* \* \* \*